(12) United States Patent
Hou et al.

(10) Patent No.: US 11,110,390 B1
(45) Date of Patent: Sep. 7, 2021

(54) SYSTEMS AND METHODS FOR TREATING STERILIZATION EXHAUST GAS CONTAINING ETHYLENE OXIDE

(71) Applicants: Chio Kang Medical, Inc., Palo Alto, CA (US); Qiaokang Biotech (Guangdong) Co., LTD., Guangzhou (CN)

(72) Inventors: Dongxin Hou, Guangzhou (CN); Jianlong Xue, Guangzhou (CN); Xiuling Zhong, Guangzhou (CN); Guqun Ren, Guangzhou (CN); Hao Chen, Guangzhou (CN); Yecheng He, Guangzhou (CN); Liqing Zhu, Guangzhou (CN); Qinghua Xiao, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

(*) Notice: Subject to any disclaimer, the term of this patent is extended or adjusted under 35 U.S.C. 154(b) by 0 days.

(21) Appl. No.: 17/002,500

(22) Filed: Aug. 25, 2020

Related U.S. Application Data (63) Continuation of application No. PCT/CN2020/100143, filed on Jul. 3, 2020.

(30) Foreign Application Priority Data

Mar. 18, 2020 (CN) .......................... 202010190366.5
Mar. 18, 2020 (CN) .......................... 202020340760.8
(Continued)

(51) Int. Cl.
*B01D 53/18* (2006.01)
*B01J 10/00* (2006.01)
(Continued)

(52) U.S. Cl.
CPC ........... *B01D 53/18* (2013.01); *B01D 53/002* (2013.01); *B01D 53/1487* (2013.01);
(Continued)

(58) Field of Classification Search
CPC ............ B01D 53/1487; B01D 53/1493; B01D 53/18; B01D 25/008; B01D 53/002;
(Continued)

(56) References Cited

U.S. PATENT DOCUMENTS

| 1,954,056 A | 4/1934 | Miller |
| 2,586,670 A | 2/1952 | Lambertsen |

(Continued)

FOREIGN PATENT DOCUMENTS

| CN | 1223166 A | 7/1999 |
| CN | 1397474 A | 2/2003 |

(Continued)

OTHER PUBLICATIONS

CN210088451U_ENG (Year: 2020).*
(Continued)

*Primary Examiner* — Jonathan Miller
*Assistant Examiner* — Gabriel E Gitman
(74) *Attorney, Agent, or Firm* — Adsero IP (57) ABSTRACT

A system for treating ethylene oxide-containing sterilization exhaust gas comprises a reaction column further comprising a column body, and an inner cavity configured to contain a liquid substrate for catalyzing ethylene oxide in ethylene oxide-containing sterilization exhaust gas; wherein the column body comprises a bottom portion having a gas inlet pipe and a liquid outlet pipe, the gas inlet pipe configured to inject the ethylene oxide-containing sterilization exhaust gas into the inner cavity and the liquid outlet pipe configured to discharge the liquid substrate from the inner cavity; and wherein, the column body comprises a top portion compris-
(Continued)

ing a gas outlet pipe having a gas inlet above a liquid level of the liquid substrate; and at least one gas distributor configured to disperse the ethylene oxide-containing sterilization exhaust gas injected from the gas inlet pipe into the inner cavity.

20 Claims, 7 Drawing Sheets (30) Foreign Application Priority Data

| Mar. 19, 2020 | (CN) | .......................... 202010194457.6 |
| Mar. 19, 2020 | (CN) | .......................... 202020348776.3 |

(51) Int. Cl.
  *A61L 2/26* (2006.01)
  *B01D 53/00* (2006.01)
  *B01D 53/14* (2006.01)
  B01D 25/00 (2006.01)
  A61L 2/20 (2006.01)
  B01F 3/04 (2006.01)

(52) U.S. Cl.
  CPC .......... *B01D 53/1493* (2013.01); *B01J 10/00* (2013.01); *A61L 2/206* (2013.01); *A61L 2/26* (2013.01); *B01D 25/008* (2013.01); *B01F 3/04531* (2013.01)

(58) Field of Classification Search
  CPC ....... B01D 53/14; B01D 53/263; A61L 2/206; A61L 2/26; B01J 10/00; B01F 3/04531; C23C 16/4412
  See application file for complete search history.

(56) References Cited

U.S. PATENT DOCUMENTS

| 2,817,689 | A | * | 12/1957 | White | .................. B01D 47/021 |
| | | | | | 585/501 |
| 3,022,054 | A | * | 2/1962 | Kotzebue | ............... B01D 3/163 |
| | | | | | 261/114.4 |
| 3,572,391 | A | * | 3/1971 | Hirsch | .................. F15D 1/0005 |
| | | | | | 138/40 |
| 3,598,543 | A | | 8/1971 | Crosby et al. | |
| 3,844,739 | A | | 10/1974 | Alfrey, Jr. | |
| 3,961,920 | A | | 6/1976 | Gilbert | |
| 3,997,633 | A | * | 12/1976 | Leva | ..................... B01D 3/328 |
| | | | | | 261/113 |
| 4,112,054 | A | * | 9/1978 | Feingold | ................ B01D 53/72 |
| | | | | | 422/34 |
| 4,119,539 | A | * | 10/1978 | Ettel | .................. B01D 21/0018 |
| | | | | | 210/800 |
| 4,134,425 | A | * | 1/1979 | Gussefeld | .............. B01J 8/0278 |
| | | | | | 137/625.3 |
| 4,243,636 | A | * | 1/1981 | Shiraki | ............... B01F 3/04531 |
| | | | | | 366/101 |
| 4,301,113 | A | * | 11/1981 | Alguire | ..................... A61L 2/24 |
| | | | | | 422/117 |
| 4,517,167 | A | * | 5/1985 | Popescu | ............. B01D 53/1487 |
| | | | | | 423/245.2 |
| 4,549,363 | A | | 10/1985 | Buonicore | |
| 4,555,251 | A | | 11/1985 | Jonsson | |
| 4,831,196 | A | * | 5/1989 | Buonicore | ............ C07C 29/106 |
| | | | | | 549/542 |
| 5,084,075 | A | | 1/1992 | Sircar | |
| 5,204,075 | A | | 4/1993 | Jain et al. | |
| 5,270,000 | A | | 12/1993 | Goldner et al. | |
| 5,283,035 | A | | 2/1994 | Karthaus et al. | |
| 5,290,345 | A | | 3/1994 | Osendorf et al. | |
| 5,511,409 | A | | 4/1996 | Knaebel | |
| 5,522,808 | A | | 6/1996 | Skalla | |
| 5,607,652 | A | | 3/1997 | Hellmuth et al. | |
| 5,641,455 | A | | 6/1997 | Rosenlund et al. | |
| 5,702,669 | A | | 12/1997 | Green et al. | |
| 5,741,470 | A | | 4/1998 | Wenzler | |
| 5,755,857 | A | | 5/1998 | Acharya et al. | |
| 5,779,773 | A | * | 7/1998 | Cam | .................. B01D 53/0423 |
| | | | | | 55/418 |
| 5,964,927 | A | | 10/1999 | Graham et al. | |
| 6,156,101 | A | | 12/2000 | Naheiri | |
| 6,684,648 | B2 | | 2/2004 | Faqih | |
| 6,743,402 | B2 | | 6/2004 | Shimakawa | |
| 7,316,733 | B1 | * | 1/2008 | Hedrick | ................. B01D 45/12 |
| | | | | | 422/147 |
| 7,625,535 | B2 | | 12/2009 | Yamaguchi | |
| 8,110,156 | B2 | | 2/2012 | Ricciardi et al. | |
| 8,431,085 | B2 | | 4/2013 | Froderberg et al. | |
| 9,616,143 | B2 | | 4/2017 | Snyder et al. | |
| 1,098,744 | A1 | | 4/2021 | Hu et al. | |
| 2002/0046569 | A1 | | 4/2002 | Faqih | |
| 2002/0197194 | A1 | | 12/2002 | Machado et al. | |
| 2005/0145108 | A1 | | 7/2005 | Rubin | |
| 2006/0236860 | A1 | | 10/2006 | Sumida et al. | |
| 2006/0249027 | A1 | | 11/2006 | Adolphsen et al. | |
| 2007/0209383 | A1 | | 9/2007 | Hutton | |
| 2008/0078289 | A1 | | 4/2008 | Sergi et al. | |
| 2008/0080999 | A1 | | 4/2008 | Bondar | |
| 2008/0289591 | A1 | | 11/2008 | Tessier et al. | |
| 2010/0196194 | A1 | * | 8/2010 | Voeten | ...................... A61L 2/24 |
| | | | | | 422/3 |
| 2011/0265644 | A1 | | 11/2011 | Swami et al. | |
| 2011/0283885 | A1 | | 11/2011 | Thiele | |
| 2012/0031268 | A1 | | 2/2012 | Yaghi et al. | |
| 2012/0298207 | A1 | | 11/2012 | Woelk et al. | |
| 2014/0119989 | A1 | | 5/2014 | Hayashi | |
| 2014/0251130 | A1 | | 9/2014 | Sprinkle et al. | |
| 2014/0290162 | A1 | | 10/2014 | Tanimoto | |
| 2016/0010883 | A1 | | 1/2016 | Jornitz et al. | |
| 2017/0056813 | A1 | | 3/2017 | McMahon et al. | |
| 2019/0076776 | A1 | | 3/2019 | Mahecha-Botero et al. | |
| 2019/0151791 | A1 | | 5/2019 | Awadh et al. | |
| 2019/0175971 | A1 | | 6/2019 | Moore et al. | |
| 2020/0148655 | A1 | | 5/2020 | Duff et al. | |

FOREIGN PATENT DOCUMENTS

| CN | 101224381 | A | | 7/2008 | | |
| CN | 101549241 | A | | 10/2009 | | |
| CN | 101773762 | A | | 7/2010 | | |
| CN | 201632182 | U | | 11/2010 | | |
| CN | 102173384 | A | | 9/2011 | | |
| CN | 102219642 | A | | 10/2011 | | |
| CN | 102302791 | A | | 1/2012 | | |
| CN | 102921570 | A | | 2/2013 | | |
| CN | 202802975 | U | | 3/2013 | | |
| CN | 202933710 | U | * | 5/2013 | .............. B01J 19/14 |
| CN | 203183363 | U | | 9/2013 | | |
| CN | 103386141 | A | | 11/2013 | | |
| CN | 103394109 | A | | 11/2013 | | |
| CN | 103394278 | A | | 11/2013 | | |
| CN | 103657383 | A | | 3/2014 | | |
| CN | 103706233 | A | | 4/2014 | | |
| CN | 203507806 | U | | 4/2014 | | |
| CN | 203564952 | U | | 4/2014 | | |
| CN | 103800926 | A | | 5/2014 | | |
| CN | 103908688 | A | | 7/2014 | | |
| CN | 203749877 | U | | 8/2014 | | |
| CN | 203750388 | U | | 8/2014 | | |
| CN | 203750389 | U | | 8/2014 | | |
| CN | 104014227 | A | | 9/2014 | | |
| CN | 104275085 | A | | 1/2015 | | |
| CN | 104307008 | A | | 1/2015 | | |
| CN | 204261680 | U | * | 4/2015 | .............. B01J 19/32 |
| CN | 204447972 | U | * | 7/2015 | .............. B01J 14/00 |
| CN | 104815535 | A | | 8/2015 | | |
| CN | 105132060 | A | | 12/2015 | | |
| CN | 105327665 | A | | 2/2016 | | |
| CN | 105664822 | A | * | 6/2016 | ........ B01F 15/00454 |
| CN | 205300112 | U | | 6/2016 | | |
| CN | 210721130 | U | | 6/2016 | | |

(56) References Cited

FOREIGN PATENT DOCUMENTS

| | | | | | |
|---|---|---|---|---|---|
| CN | 106139199 | A | | 11/2016 | |
| CN | 106421844 | A | | 2/2017 | |
| CN | 106475021 | A | * | 3/2017 | ............ B01J 10/00 |
| CN | 106582126 | A | | 4/2017 | |
| CN | 206443946 | U | | 8/2017 | |
| CN | 206535551 | U | | 10/2017 | |
| CN | 206853397 | U | | 1/2018 | |
| CN | 107677016 | A | | 2/2018 | |
| CN | 207169397 | U | | 4/2018 | |
| CN | 207187436 | U | | 4/2018 | |
| CN | 207356290 | U | | 5/2018 | |
| CN | 207745676 | U | | 8/2018 | |
| CN | 207913454 | U | | 9/2018 | |
| CN | 108607511 | A | | 10/2018 | |
| CN | 208047841 | U | | 11/2018 | |
| CN | 208218734 | U | | 12/2018 | |
| CN | 109382064 | A | | 2/2019 | |
| CN | 208448985 | U | | 2/2019 | |
| CN | 208893903 | U | | 5/2019 | |
| CN | 110145747 | A | | 8/2019 | |
| CN | 110302634 | A | | 10/2019 | |
| CN | 110404485 | A | | 11/2019 | |
| CN | 110461371 | A | | 11/2019 | |
| CN | 209662917 | U | | 11/2019 | |
| CN | 110833754 | A | | 2/2020 | |
| CN | 210021633 | U | | 2/2020 | |
| CN | 210088451 | U | * | 2/2020 | ............ B01D 53/02 |
| DE | 4236622 | C1 | | 3/1994 | |
| EP | 0130319 | A2 | | 1/1985 | |
| EP | 0350677 | A1 | | 1/1990 | |
| EP | 1302478 | A1 | | 4/2003 | |
| GB | 1472091 | A | * | 4/1977 | ............ B01D 53/18 |
| JP | 2008114210 | A | | 5/2008 | |
| JP | 2013172790 | A | | 10/2016 | |
| JP | 2010259648 | A | | 5/2018 | |
| NO | 2883598 | A1 | * | 6/2015 | ............ B01D 61/18 |
| WO | WO2011002277 | A1 | | 1/2011 | |
| WO | WO-2019-136504 | A1 | | 7/2019 | |
| WO | WO2019236249 | A1 | | 12/2019 | |

OTHER PUBLICATIONS

Kähm, W., & Vassiliadis, V. V. (2018). Lyapunov exponents with Model Predictive Control for exothermic batch reactors. IFAC-PapersOnLine, 51(18), 423-428. (Year: 2018).*
CN106475021A_ENG Espacenet machine translation of Zhengzhou) (Year: 2017).*
CN204261680U_ENG (Espacenet machine translation of Wang) (Year: 2015).*
CN210088451U_ENG (Espacenet machine translation of Zheng) (Year: 2020).*
CN106475021A_ENG (Espacenet machine translation of Zhengzhou Aimofu) (Year: 2017).*
Kähm et al. (2018, Lyapunov exponents with Model Predictive Control for exothermic batch reactors, IFAC-PapersOnLine, 51(18), 423-428) (Year: 2018).*
CN204447972U_ENG (Espacenet machine translation of Li) (Year: 2015).*
CN105664822A_ENG (Espacenet machine translation of Zhou) (Year: 2016).*
CN202933710U_ENG (Espacenet machine translation of Zhang) (Year: 2013).*
International Application No. PCT/CN2020/101140 as prepared by the Chinese International Searching Authority filed on Jul. 9, 2020, 59 pages.
U.S. Appl. No. 17/012,857, TrackOne Bypass CON Application, filed Sep. 4, 2020, 148 pages.
International Application No. PCT/CN2020/100143 as prepared by the Chinese International Searching Authority filed on Jul. 3, 2020, 25 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
U.S. Appl. No. 17/002,529, TrackOne Bypass CON Application filed Aug. 25, 2020, 64 pages.
International Application No. PCT/CN2020/100119 as prepared by the Chinese International Searching Authority filed on Jul. 3, 2020, 29 pages.
U.S. Appl. No. 17/002,540, TrackOne Bypass CON Application filed Aug. 25, 2020, 89 pages.
International Application No. PCT/CN2020/100120 as prepared by the Chinese International Searching Authority filed on Jul. 3, 2020, 28 pages.
U.S. Appl. No. 17/004,730, TrackOne Bypass CON Application filed Aug. 27, 2020, 77 pages.
International Application No. PCT/CN2020/101142 as prepared by the Chinese International Searching Authority filed on Jul. 9, 2020, 29 pages.
U.S. Appl. No. 17/012,864, TrackOne Bypass CON Application filed Sep. 4, 2020, 78 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
U.S. Appl. No. 17/004,930, TrackOne Bypass CON Application filed Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed on Jul. 3, 2020, 35 pages.
U.S. Appl. No. 17/004,971, TrackOne Bypass CON Application filed Aug. 27, 2020, 75 pages.
U.S. Appl. No. 17/012,857, Non-Final Office Action, dated Nov. 24, 2020, 13 pages.
U.S. Appl. No. 17/002,540, Office Action-Restriction Requirement, dated Dec. 1, 2020, 7 pages.
U.S. Appl. No. 17/004,971, Office Action-Restriction Requirement, dated Dec. 9, 2020, 6 pages.
U.S. Appl. No. 17/002,523 Notice of Allowance, dated Dec. 17, 2020, 35 pages.
U.S. Appl. No. 17/004,930 Office Action-Restriction Requirement, dated Dec. 18, 2020, 8 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.

(56) References Cited

OTHER PUBLICATIONS

International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/004,971, Notice of Allowance, dated Feb. 8, 2021, 30 pages.
U.S. Appl. No. 17/002,529, Non-Final Office Action-Restriction Requirement dated Feb. 17, 2021, 11 pages.
U.S. Appl. No. 17/012,857, Notice of Allowance, dated Mar. 1, 2021, 26 pages.
U.S. Appl. No. 17/004,730, Non-Final Office Action-Restriction Requirement dated Mar. 1, 2021, 7 pages.
U.S. Appl. No. 17/002,540, Final Office Action, dated Mar. 26, 2021, 36 pages.
U.S. Appl. No. 17/004,730, Non-Final Office Action, dated Apr. 1, 2021, 30 pages.
U.S. Appl. No. 17/002,540, Notice of Allowance, dated Apr. 26, 2021, 21 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.
U.S. Appl. No. 17/004,930 Notice of Allowance, dated Apr. 28, 2020, 35 pages.
U.S. Appl. No. 17/004,903 Notice of Allowance, dated May 17, 2021, 20 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.

* cited by examiner

SYSTEMS AND METHODS FOR TREATING STERILIZATION EXHAUST GAS CONTAINING ETHYLENE OXIDE

CROSS-REFERENCE TO RELATED PATENT APPLICATIONS

This application is a continuation of International Application No. PCT/CN2020/100143, filed on Jul. 3, 2020, which claims the benefit of Chinese Patent Application No. CN202010194457.6, filed on Mar. 19, 2020, Chinese Patent Application No. CN202020348776.3, filed on Mar. 19, 2020, Chinese Patent Application No. CN202010190366.5 filed on 18 Mar. 2020, and Chinese Patent Application No. CN202020340760.8, filed on Mar. 18, 2020, the entire contents of which are incorporated herein by reference in their entireties for all purposes.

TECHNICAL FIELD

The disclosure relates to the technical field of sterilization technology, and more particularly, to a system and method for treating sterilization exhaust gas containing ethylene oxide.

BACKGROUND

Ethylene oxide ("EO") is a broad-spectrum, high-efficiency sterilization agent with excellent performance. Ethylene oxide has a strong penetration force, can kill various microorganisms at ambient temperature, and does not damage the article subject to sterilization. Sterilization by ethylene oxide gas is currently one of the predominant cryogenic sterilization methods, especially in hospitals.

After sterilization with ethylene oxide gas, the gas used for sterilization must be exhausted (referred to as the "sterilization exhaust gas"). However, ethylene oxide itself is toxic, flammable, and explosive. Thus, the sterilization exhaust gas generated in the sterilizer is typically subject to decontamination treatment before discharge. Conventional treatments of ethylene oxide-containing sterilization exhaust gas include: (1) a catalytic combustion method, in which the sterilization exhaust gas is subjected to catalytic combustion to form a non-toxic substance, but, because ethylene oxide is flammable and explosive, this process presents a potential safety hazard in the treatment of sterilization exhaust gas; (2) an absorption method, in which ethylene oxide is directly absorbed by water or is treated by water added with sulfuric acid or hydrochloric acid to catalyze the reaction of water with ethylene oxide to form ethylene glycol, but current implementations for carrying out the absorption method have poor treatment performance; and (3) a low-temperature recovery method, in which ethylene oxide is recovered after the sterilization exhaust gas is condensed at a temperature of −29 degrees Celsius, but this method has high energy consumption and very high requirements for equipment.

Accordingly, tools and techniques for the improved treatment of sterilization exhaust gas including ethylene oxide are provided.

SUMMARY

In one aspect, a system for treating ethylene oxide-containing sterilization exhaust gas is provided. The system comprises a reaction column, and the reaction column comprises a column body and at least one gas distributor. The column body includes an inner cavity configured to contain a liquid substrate; a bottom portion, the bottom portion further comprising a gas inlet pipe and a liquid outlet pipe, wherein the gas inlet pipe is configured to inject the ethylene oxide-containing sterilization exhaust gas into the inner cavity and the liquid outlet pipe is configured to discharge the liquid substrate from the inner cavity; and a top portion further comprising a gas outlet pipe, wherein the gas outlet pipe includes a gas inlet that is above a liquid level of the liquid substrate. The at least one gas distributor is disposed in the inner cavity of the column body and above a gas outlet of the gas inlet pipe. The at least one gas distributor is configured to disperse the ethylene oxide-containing sterilization exhaust gas injected from the gas inlet pipe into the inner cavity.

In another aspect, a method of treating ethylene oxide-containing sterilization exhaust gas is provided. The method comprises, at step (S101), providing a reaction column comprising an inner cavity; containing a liquid substrate within the inner cavity of the reaction column, wherein the reaction column further includes a gas outlet pipe which includes a gas inlet disposed above a liquid level of the liquid substrate, and at least one gas distributor disposed below the liquid level of the liquid substrate. The method continues, at step (S102) injecting ethylene oxide-containing sterilization exhaust gas into a gas inlet pipe, pressurizing, via a pressurizer, the ethylene oxide-containing sterilization exhaust gas in the gas inlet pipe, injecting the pressurized ethylene oxide-containing sterilization exhaust gas into the inner cavity, wherein the ethylene oxide-containing sterilization exhaust gas is brought into contact with the liquid substrate, and wherein injecting the pressurized ethylene oxide-containing sterilization exhaust gas into the inner cavity further comprises dispersing, via the at least one gas distributor, the ethylene oxide-containing sterilization exhaust gas in the inner cavity, and discharging, via the gas outlet pipe the ethylene oxide-containing sterilization exhaust gas that has passed through the liquid substrate. The method further includes, at step (S103) discharging the liquid substrate through a liquid outlet pipe of the reaction column, when treatment capacity of the liquid substrate for the ethylene oxide-containing sterilization exhaust gas is reduced to a threshold level of catalyzing effectiveness.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
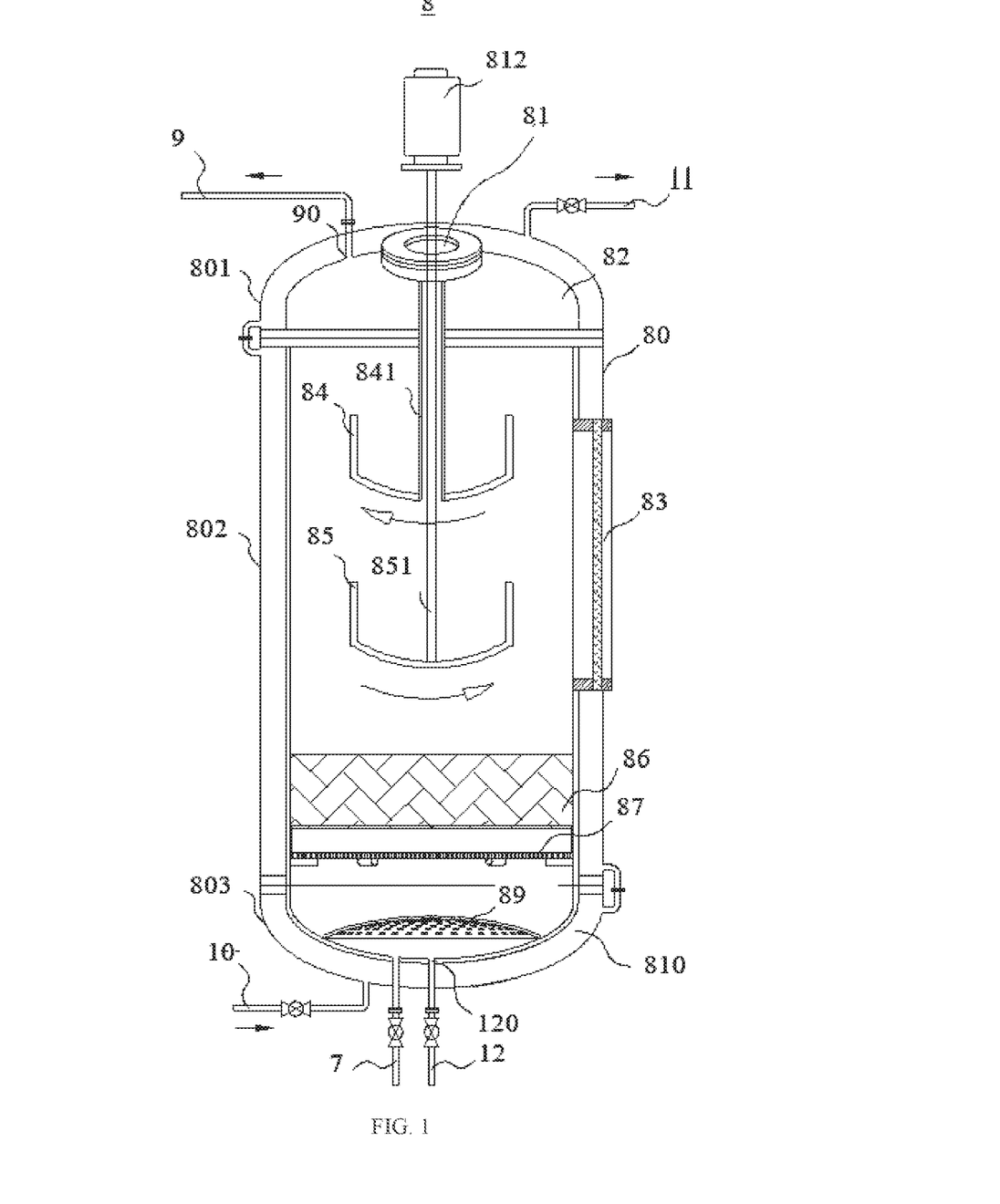
FIG. 1 schematically shows a cross-sectional view of a reaction column according to an embodiment of the present disclosure.

FIG. 1 shows a cross-sectional view of a reaction column 8 in a system for treating sterilization exhaust gas containing ethylene oxide according to an embodiment of the present disclosure.

The reaction column 8 may include a column body 80 with an inner cavity 82 that contains a liquid substrate for catalyzing ethylene oxide (EO) in EO-containing sterilization exhaust gas (also referred to herein interchangeably as "sterilization exhaust gas" or simply "exhaust gas") to react with water. The bottom of the column body 80 (also referred to as a "bottom portion" or "lower portion") comprises a gas inlet pipe 12 and a liquid outlet pipe 7. EO-containing sterilization exhaust gas may be injected via the gas inlet pipe 12 into the bottom of the inner cavity 82 where the liquid substrate can catalyze EO in EO-containing sterilization exhaust gas to react with water to generate ethylene glycol. The liquid outlet pipe 7 is used to discharge the liquid substrate out of the inner cavity 82 for replacement of the liquid substrate. The top of the column body 80 (also referred to as "top portion" or "upper portion") is provided with a gas outlet pipe 9 with a gas inlet 90 which is above the liquid level of the liquid substrate, wherein residual gas after passing through the liquid substrate is discharged through the gas outlet pipe 9. At least one gas distributor, such as a first gas distributor 89, is provided in the inner cavity 82 above a gas outlet 120 of the gas inlet pipe 12 for dispersing the EO-containing sterilization exhaust gas injected from the gas inlet pipe 12 into the inner cavity 82. The at least one gas distributor may be configured to disperse the EO-containing exhaust gas, from the gas inlet pipe 12, evenly within the inner cavity 82, and thereby increasing contact between the EO-containing exhaust gas and the liquid substrate, diffusing the EO-containing exhaust gas in the liquid substrate, and improving efficiency in ethylene oxide treatment.

The column body 80 in this example may comprise, for example, an upper sealing cover 801, a cylindrical body 802, and a lower sealing cover 803 assembled together. Each of the upper sealing cover 801 and the lower sealing cover 803 may be coupled to an upper portion (e.g., top) and a lower portion (e.g., bottom) of the cylindrical body 802, respectively. In some embodiments, a seal may be formed between the cylindrical body 802 and each of the upper sealing cover 801 and lower sealing cover 803. Accordingly, each of the upper sealing cover 801 and lower sealing cover 803 may be configured to form a respective seal circumferentially around the respective upper and lower portions of the cylindrical body 820 in contact with the upper sealing cover 801 and lower sealing cover 803 when in a closed position. The seal may be configured to prevent liquid, gas, or both liquid and gas from passing through the seal.

The liquid substrate contained in the inner cavity 82 may, for example, be a liquid acid substrate configured to physically adsorb ethylene oxide and chemically react with ethylene oxide to produce alcohol, thereby decontaminating ethylene oxide in the sterilization exhaust gas efficiently to reduce environmental pollution. In some embodiments, the liquid acid substrate may include, for example, an ethylene oxide catalytic concentrate. According to some embodiments, the ethylene oxide catalytic concentrate may be mainly composed of a combination of inorganic acids, sulfonic acids, and unsaturated fatty acids. In some cases, the molar ratio of inorganic acids to sulfonic acids to oleic acids may range from 1:1:1 to 1:1000:100, or the like. Alternatively, the ethylene oxide catalytic concentrate may include one or two of inorganic acids, sulfonic acids, or unsaturated fatty acids. In some embodiments, the inorganic acids may include, without limitation, at least one of sulfuric acid or phosphoric acid, and/or the like. According to some embodiments, the sulfonic acids may have a general formula of $R-SO_3H$, where R is a hydrocarbyl, and may include, but are not limited to, at least one of methylsulphonic acid, ethylsulfonic acid, propylsulfonic acid, butylsulfonic acid, pentylsulfonic acid, hexylsulfonic acid, heptylsulfonic acid, octylsulfonic acid, nonylsulfonic acid, decylsulfonic acid, undecylsulfonic acid, dodecylsulfonic acid, tridecylsulfonic acid, tetradecylsulfonic acid, pentadecylsulfonic acid, hexadecylsulfonic acid, heptadecylsulfonic acid, octadecylsulfonic acid, methylsulfonic acid, ethylbenzenesulfonic acid, propylbenzenesulfonic acid, butylbenzenesulfonic acid, pentylbenzenesulfonic acid, hexylbenzenesulfonic acid, heptybenzenesulfonic acid, octylbenzenesulfonic acid, nonylbenzenesulfonic acid, decylbenzenesulfonic acid, undecylbenzenesulfonic acid, dodecylbenzenesulfonic acid, tridecylbenzenesulfonic acid, tetradecylbenzenesulfonic acid, pentadecylbenzenesulfonic acid, hexadecylbenzenesulfonic acid, heptadecylbenzenesulfonic acid, octadecylbenzenesulfonic acid, nonadecylbenzenesulfonic acid, or eicosylbenzenesulfonic acid, and/or the like. Merely by way of example, in some cases, the unsaturated fatty acids might include, without limitation, at least one of oleic acid, linoleic acid, or linolenic acid, and/or the like.

On the one hand, the strong acidity of the ethylene oxide catalytic concentrate allows it to catalyze the reaction of the EO-containing sterilization exhaust gas to synthesize ethylene glycol, and on the other hand, the surfactant property of the ethylene oxide catalytic concentrate allows it to react with EO-containing sterilization exhaust gas to produce a compound complex, therefore increasing efficiency of adsorption of the EO-containing sterilization exhaust gas by the ethylene oxide catalytic concentrate, thereby improving treatment efficiency of the EO-containing sterilization exhaust gas, ensuring safety and reliability of the treatment process of the EO-containing sterilization exhaust gas, and yielding high treatment performance (relative to treatment by a solution of water and single acid) and low environmental pollution.

Figure 2:
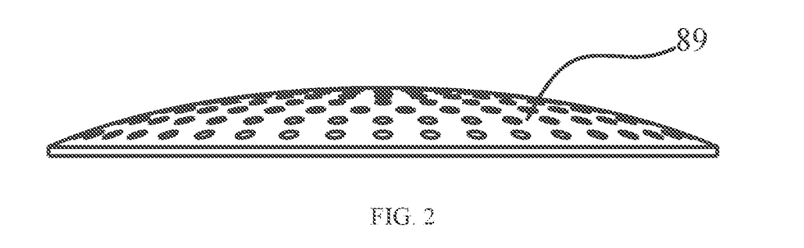
FIG. 2 shows a front view of the first gas distributor of FIG. 1.
Figure 3:
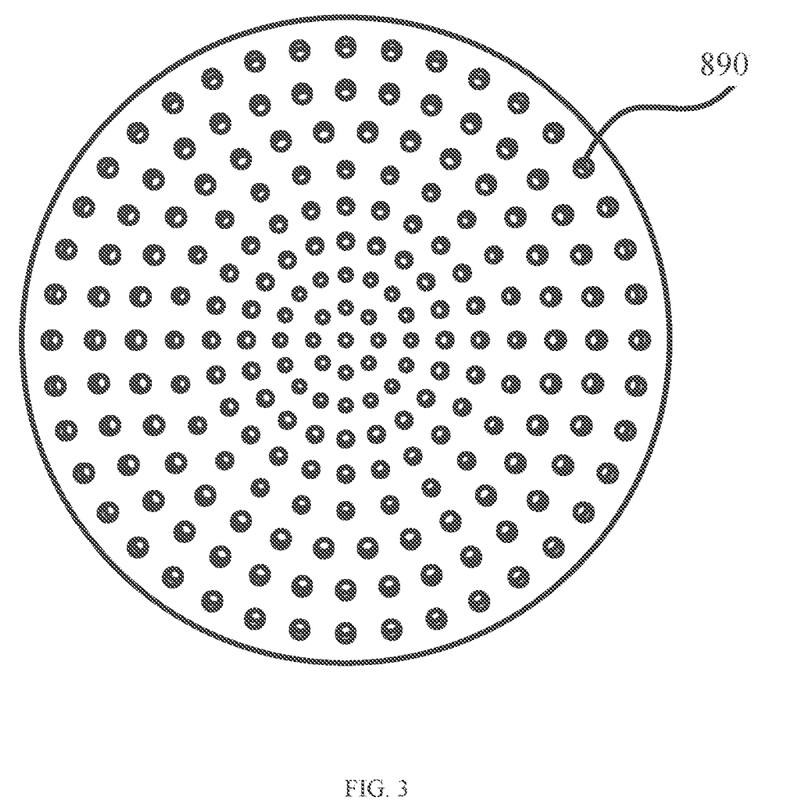
FIG. 3 shows a top view of the first gas distributor of FIG. 1.

In some embodiments, referring to FIGS. 2 and 3, the at least one gas distributor may include a first gas distributor 89. The first gas distributor 89 may comprise a curved plate with a high center, pointing inward towards the cylindrical body 802, and curving lower moving from the center to the edge of the curved plate. In some embodiments, the edge may be coupled to a bottom wall of the inner cavity 82. In further embodiments, the curved plate may further be coupled to an inner wall of the lower sealing cover 803. In some embodiments, the curved plate may comprise a plurality of first air holes 890, each of the plurality of first air holes 890 being circular in shape, and distributed in an annular arrangement. For example, in some embodiments, the curved plate may include one or more concentric rings of airholes, radiating from the center outward towards the edges. Thus, the gas inlet pipe 12 may be in fluid communication with the gas outlet pipe 9 via the plurality of first air holes 890. In some embodiments, moving from the center to the edge of the curved plate, the hole size of the plurality of first air holes 890 may gradually increase. Thus, in some examples, air holes closer to the center of the curved plate are smaller in size than air holes that are closer to the edge of the curved plate. In some of the examples, moving from the center to the edge of the curved plate, the plurality of first air holes 890 may gradually increase in hole pitch. In other words, continuing with the example of one or more concentric rings of air holes, the distance between air holes may increase in a given concentric ring the further away the concentric ring is from the center of the curved plate. Thus, in the above examples, the plurality of first air holes 890 may be configured to evenly distribute, in the inner cavity 82, the EO-containing sterilization exhaust gas as it is injected into the inner cavity 82 through the first gas distributor 89.

Figure 4:
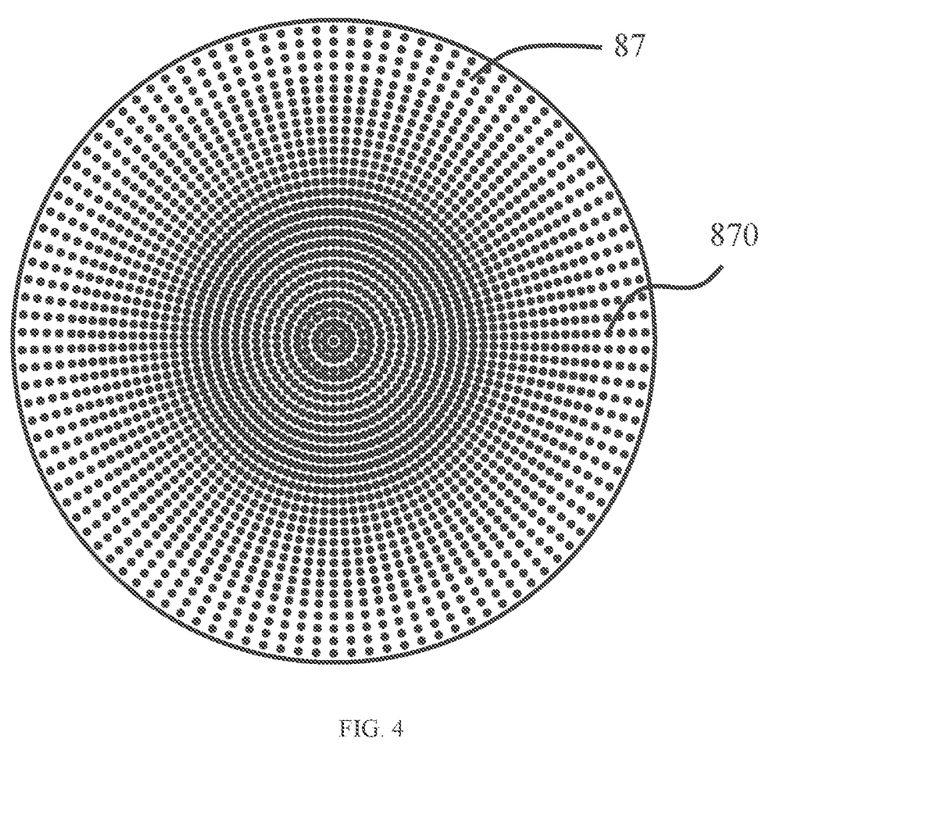
FIG. 4 shows a top view of the second gas distributor of FIG. 1.

In some of the examples, referring to FIG. 4, the at least one gas distributor may further include a second gas distributor 87, which may be a flat plate with an edge connected to a side wall of the inner cavity 82. The flat plate may be located above the curved plate (closer to the center of the inner cavity 82), and further coupled to an inner wall of the cylindrical body 802. The flat plate may include a plurality of second air holes 870, each of the plurality of second air holes 870 being circular in shape, and in an annular arrangement. Moving from the center to the edge of the flat plate, the plurality of second air holes 870 may be configured to gradually increase in hole pitch. In some examples, each of the plurality of second air holes 870 may be the same in hole size. The plurality of second air holes 870 may specifically designed to further evenly disperse the EO-containing sterilization exhaust gas by diffusing the release of the EO-containing sterilization exhaust gas into the liquid substrate, further increasing the contact area between the EO-containing sterilization exhaust gas and the liquid substrate.

Figure 5:
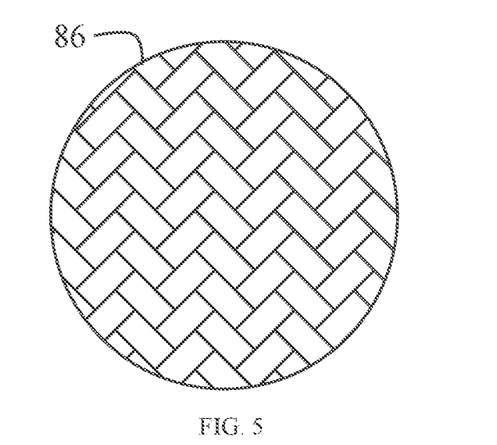
FIG. 5 is a partially enlarged view of the filter screen of FIG. 1.

With reference to FIGS. 1 and 5, the reaction column 8 may further include a filter screen 86 located in the inner cavity 82. The filter screen 86 may be removably coupled to the side wall of the inner cavity 82 and located above the at least one gas distributor (e.g., the first gas distributor 89 and/or the second gas distributor 87). The filter screen 86 may further be coupled to the inner wall of the cylindrical body 802. In some embodiments, the filter screen 86 may be a multi-layer mesh structure. The filter screen 86 may be configured to filter and evenly disperse EO-containing sterilization exhaust gas, uniformly mixing the EO-containing sterilization exhaust gas with the acid substrate. The filter screen 86 may, in some embodiments, be configured to be periodically replaced or maintained (e.g., removed and cleaned). It is to be understood that the above gas distributors 87, 89 and filter screen 86 are all disposed below the working liquid level of the liquid substrate (e.g., below a threshold effective amount of liquid substrate) and are submerged in the liquid substrate.

Referring again to FIG. 1, the reaction column 8 may further include two stirrers 84, 85 disposed in the inner cavity 82, each stirrer being located above the filter screen 86 and configured to stir the liquid substrate. A primary stirrer 85 may be connected to a first rotating shaft 851, wherein an upper end of the first rotating shaft 851 extends out of the column body 80 and is coupled to a first driver 812. The first driver 812 may, for example, include, without limitation, a motor, actuator, or other suitable device for driving the primary stirrer 85. The secondary stirrer 84 may be positioned above the primary stirrer 85 and coupled to a second rotating shaft 841, wherein the upper end of the second rotating shaft 841 extends out of the upper sealing cover 801 of the column body 80 and is coupled to a second driver. The second driver, like the first driver 812, may similarly include, without limitation, a motor, actuator, or other suitable device for driving the secondary stirrer 84. The second rotating shaft 841 may be disposed coaxially with the first rotating shaft 851.

In some examples, the primary stirrer 85 may be configured to rotate in a first rotation direction. The secondary stirrer 84 may be configured to rotate in a second rotation direction that is opposite to a first rotation direction of the primary stirrer 85. In some examples, the first driver 812 and the second driver may be the same driver. For example, the first driver 812 may be configured to be selectively connected to the first rotating shaft 851 and the second rotating shaft 841. Alternatively, a mechanical coupling may be provided between the first rotating shaft 851 and the second rotating shaft 841, such that when the first driver 812 is activated, the mechanical coupling is configured to cause the first rotating shaft 851 and the second rotating shaft 841 to contra-rotate synchronously, thereby causing the primary stirrer 85 and the secondary stirrer 84 to contra-rotate synchronously to agitate the liquid substrate. Accordingly, the mechanical coupling may include, without limitation, one or more gears, a transmission, or other mechanical coupling as known to those skilled in the art. In some embodiments, the mechanical coupling may be coupled directly to the first driver 812, with each of the first rotating shaft 851 and second rotating shaft 841 coupled to the first driver 812 via the mechanical coupling. Alternatively, the first driver 812 may be coupled to one of the first rotating shaft 851 or second rotating shaft 841. The mechanical coupling may, in turn, couple the shaft coupled to the first driver 812 to the other shaft that is not coupled directly to the first driver 812.

It is to be understood that in some further embodiments, the reaction column 8 may comprise an alternative arrangement utilizing a single primary stirrer, or alternatively three or more stirrers may be provided in the inner cavity 82.

Returning to FIG. 1, in some embodiments, the column body 80 may further include a sandwich chamber 810 surrounding the inner cavity 82, and a coolant inlet pipe 10 and coolant outlet pipe 11 in fluid communication with the sandwich chamber 810. Thus, in some embodiments, coolant may be allowed to enter the sandwich chamber 810 from the coolant inlet pipe 10, exit from the coolant outlet pipe 11, and recycled so as to cool the reaction column 8. The coolant may include, without limitation, water (including tap water, distilled water, deionized water, heavy water, and the like), antifreeze, oils, liquefied gas, or other fluid coolant as known to those skilled in the art. In some examples, water may be utilized as a coolant, with the water temperature being controlled to be between, for example, 20° C.~30° C. In some embodiments, the reaction column 8 may further include a cooling device for cooling the column body 80 of the reaction column 8, wherein the cooling device coupled to the coolant inlet pipe 10 and/or the coolant outlet pipe 11. In some examples, the cooling device may include, for example, a water storage tank, a water pump, and a circulating water pipe, with the circulating water pipe communicatively coupling the coolant inlet pipe 10 and a coolant outlet pipe 11, respectively, with the water storage tank, and the water pump being mounted on the circulating water pipe and configured to circulate the water. In yet further embodiments, the cooling device may further include a cooler coupled to one or more of the water storage tank or circulating water pipe. The cooling device may include, without limitation, a heat pump, thermoelectric cooler, vapor compression cooler, or other cooling device as known to those skilled in the art.

In some of the examples, the column body 80 is provided with a top viewer 81 and/or a side-wall viewer 83. The top viewer 81 and/or side-wall viewer 83 may, for example, be windows into the inner cavity 82. The top viewer 81 may be fixed, for example, to the top of the upper sealing cover 801 around the first rotating shaft 851 and the second rotating shaft 841. The side wall viewer 83 may, for example, be fixed to the cylindrical body 802. In some embodiments, the top viewer 81 and the side-wall viewer 83 may be, for example, made of a transparent material. For example, the top viewer 81 and side-wall viewer 83 may be made from glass or a polymeric material, such as polycarbonate, acrylonitrile butadiene styrene, polyurethane, acrylic, or other suitable materials.

Figure 6:
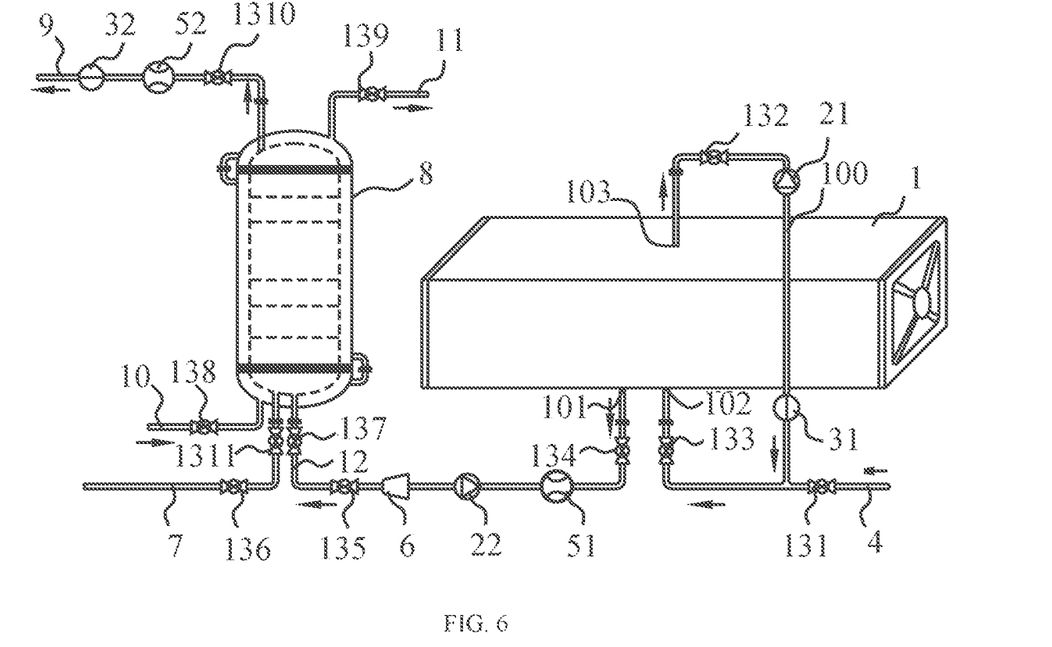
FIG. 6 shows a schematic diagram of a system for treating ethylene oxide-containing sterilization exhaust gas according to an embodiment of the present disclosure.

With reference to FIG. 6, in some embodiments, a first flow meter 52 and a first EO concentration detector 32 may be operatively coupled to the gas outlet pipe 9. The first flow meter 52 may be configured to detect and regulate gas flow through the gas outlet pipe 9. The first EO concentration detector 32 may be configured to detect the EO concentration of gas in the gas outlet pipe 9, with detection mechanisms including electrochemical, PID and thermal conductivity detection.

In some of the examples, the system may further comprise a sterilizer 1 with an output port 101 that coupled to the gas inlet pipe 12. In various embodiments, the sterilizer 1 may be an EO sterilizer. The sterilizer 1 may comprise a gas inlet 102 coupled to an input pipe 4, the gas inlet 102 configured to inject EO-containing sterilizing gas into the sterilizer 1. The sterilizer 1 may, thus, be configured to sterilize articles contained within the sterilizer 1 utilizing the EO-containing sterilizing gas. EO-containing sterilization exhaust gas, remaining after the sterilization process, may be discharged from the output port 101 into the gas inlet pipe 12 to supply the EO-containing sterilization exhaust gas to the reaction column 8.

In some of the examples, the gas inlet pipe 12 may be coupled, sequentially, to a second flow meter 51, a first gas extractor 22, and a pressurizer 6 in the flow direction. The second flow meter 51 may be configured to detect and regulate the intake air flow through the gas inlet pipe 12. The first gas extractor 22 may be configured to extract the sterilization exhaust gas from the sterilizer 1 and inject the sterilization exhaust gas into the inner cavity 82 of the reaction column 8. Thus, the first gas extractor 22 may include, for example, a vacuum pump or other suitable fluid pump configured to pump gas from the sterilizer 1 into the inner cavity 82 of the reaction column 8. The pressurizer 6 may be configured to pressurize the sterilization exhaust gas in the gas inlet pipe 12 that will enter the inner cavity 82. The pressurizer 6 may include, for example, a booster pump, such as a gas booster pump, and the power gas may be, for example, nitrogen gas.

In some embodiments, the sterilizer 1 may further comprise a gas circulation line 100, which is coupled to the gas inlet 102 and a gas outlet 103 of the sterilizer 1, respectively. A second gas extractor 21 and a second EO concentration detector 31 may be operatively coupled to the gas circulation line 100. The second gas extractor 21 may be, for example, a vacuum pump. By activating the second gas extractor 21, the EO-containing sterilizing gas is allowed to circulate through the sterilizer 1 and the gas circulation line 100 to sterilize articles in the sterilizer 1, thereby generating EO-containing sterilization exhaust gas. The second EO concentration detector 31 may be configured to detect the EO concentration of the gas in the gas circulation line 100, wherein its detection mechanisms include electrochemical, PID and thermal conductivity detection.

As can be seen from FIG. 1 and FIG. 6, in order to control the ON and OFF state of each line in the system, valves may be respectively provided on each line. For example, a valve 131 is operatively coupled to the input pipe 4, upstream of the gas circulation line 100, and a valve 133 coupled to the input pipe 4 at a position downstream of the junction between input pipe 4 and gas circulation line 100, and upstream of the gas inlet 102. Valve 132 is coupled to the gas circulation line 100, upstream of the junction with the input pipe 4, and downstream of the gas outlet 103. In some embodiments, multiple valves may be coupled to the gas inlet pipe 12. Valve 134 may be coupled to the gas inlet pipe 12, downstream of the outlet port 101 of the sterilizer 1, and upstream of at least one of the second flow meter 51, first gas extractor 22, and pressurizer 6. Valve 135 may be coupled to the inlet pipe 12 downstream of the pressurizer 6 and upstream of valve 137. Valve 137 may be located downstream of the valve 135, and upstream of the gas outlet 120. Similarly, multiple valves may be coupled to the liquid outlet pipe 7. Valve 1311 may be located downstream of the inner cavity 82 and upstream of the valve 136. Valve 138 may be coupled to the coolant inlet pipe 10, and a valve 139 may be coupled to the coolant outlet pipe 11. A valve 1310 may be coupled to the gas outlet pipe 9. In some embodiments, each of the valves may be, for example, an electric valve configured to be automatically controlled, for example, by a controller or other electrical signal. In other embodiments, the valves may include other types valves, such as manually actuated valves, hydraulic valves, and the like.

In some embodiments, the treatment system may be powered by a solar power system. Thus, in some embodiments, one or more of the reaction column 8, sterilizer 1, or individual components of the treatment system may be coupled to a solar power system, and may be configured to be powered by the solar power system.

Figure 7:
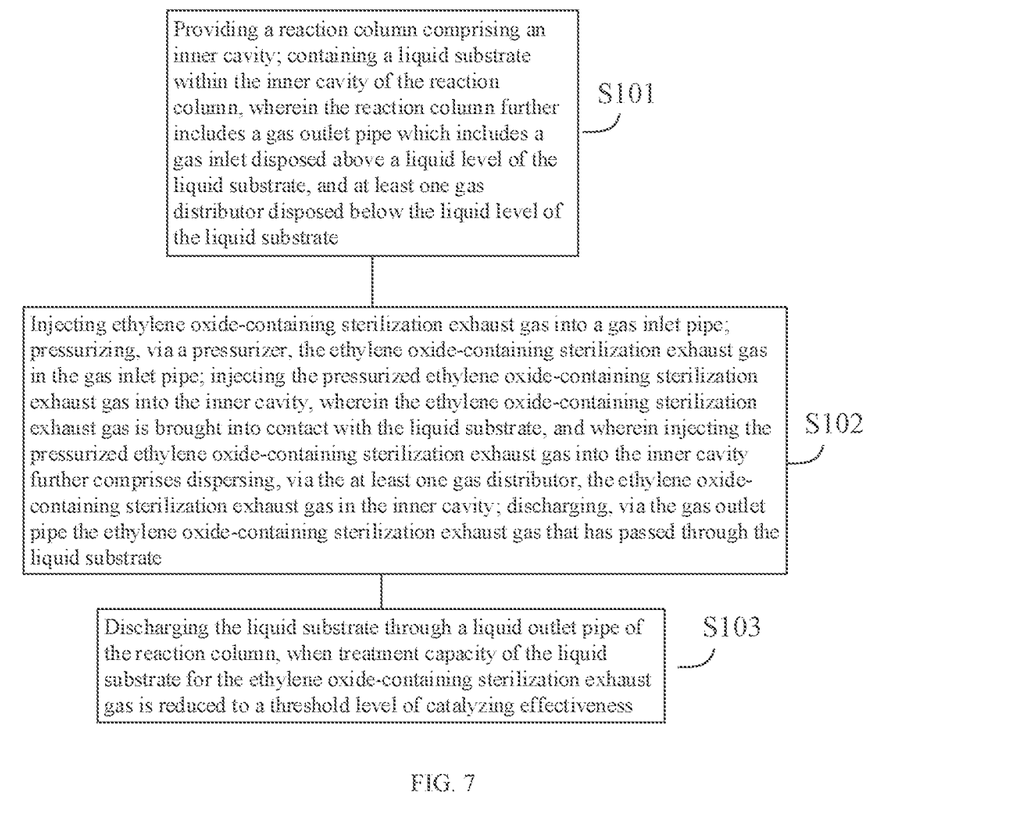
FIG. 7 shows a flowchart of a method for treating ethylene oxide-containing sterilization exhaust gas according to an embodiment of the present disclosure.

Referring to FIG. 7, according to an example, a method of treating ethylene oxide-containing sterilization exhaust gas is provided, comprising the following steps:

At block S101, the above described system is provided, wherein the liquid substrate is contained in the inner cavity 82 of the reaction column 8, the gas inlet 90 is above a liquid level of the liquid substrate, and at least one gas distributor is below the liquid level of the liquid substrate. As previously described, the liquid substrate may include, for example, the ethylene oxide catalytic concentrate.

At block S102, the ethylene oxide-containing sterilization exhaust gas is injected into the gas inlet pipe 12, the ethylene oxide-containing sterilization exhaust gas in the gas inlet pipe 12 is pressurized through a pressurizer 6, and the pressurized ethylene oxide-containing sterilization exhaust gas is injected into the inner cavity 82 passing through and coming into contact with the liquid substrate. The flow rate of ethylene oxide-containing sterilization exhaust gas may be controlled by the second flow meter 51, and/or one or more valves 134, 135, 137.

In some embodiments, at least one gas distributor may be configured to disperse the ethylene oxide-containing sterilization exhaust gas injected into the inner cavity 82. In some further embodiments, the reaction column 8 may comprise one or more stirrers configured to stir the liquid substrate. As previously described, in some embodiments, a pair of stirrers may be utilized in the reaction column 8, each stirrer configured to have opposite stirring directions (e.g., contra-rotating). In some embodiments, the treatment progress in the reaction column 8 may be monitored in real-time through the top viewer 81 and/or the side wall viewer 83.

The EO-containing sterilization exhaust gas, after passing through the liquid substrate, may be discharged from the inner cavity 82 via gas inlet 90, and carried downstream by the gas outlet pipe 9. The gas flow rate in the gas outlet pipe 9 may be monitored and controlled by the first flow meter 52. The first EO concentration detector 32 may be configured to detect the EO concentration in the gas outlet pipe 9. After gas in the reaction column 8 is discharged, the reaction column 8 may be cooled down via coolant passed through the sandwich chamber 810.

At S103, the liquid substrate may be discharged through the liquid outlet pipe 7, when treatment capacity of the liquid substrate for the EO-containing sterilization exhaust gas is reduced by a certain degree. For example, in some embodiments, the liquid substrate may be drained and replaced with new liquid substrate when a treatment capacity of the liquid substrate reaches a threshold level of catalyzing effectiveness. In one example, a threshold level of catalyzing effectiveness may be reached when the mass ratio of EO to the liquid substrate reaches 3:10.

In further embodiments, a method of using the above described treatment system to treat EO-containing sterilization exhaust gas comprises the following steps:

At step S1, the lower sealing cover 803 may be coupled to the cylindrical body 802 to create a seal between the surfaces of the lower sealing cover 803 in contact with the surfaces of the cylindrical body 802. In some embodiments, the lower sealing cover 803 and/or the cylindrical body 802 may include one or more of a sealing gasket and flange. Thus, a seal may be created between the sealing gasket and the flange. A liquid acid substrate may be injected into the inner cavity 82, through a liquid inlet, or poured into an opening at the top of cylindrical body 802. In some further embodiments, the liquid substrate may be introduced into the inner cavity 82 via the liquid outlet pipe 7. Thus, in some embodiments, the liquid outlet pipe 7 may be configured to both fill and drain the liquid substrate from the inner cavity 82. Once filled with the liquid substrate, the upper sealing cover 801 may be closed. Thus, like the lower sealing cover 803, the upper sealing cover 801 may similarly be coupled to the cylindrical body 802 to create a seal, for example, via a respective sealing gasket and flange.

At step S2, the EO-containing sterilization exhaust gas may be extracted by the first gas extractor 22, and valve 134, valve 135, and valve 137 opened. The flow rate of the EO-containing sterilization exhaust gas may be regulated by the second flow meter 51. The EO-containing sterilization exhaust gas may be pressurized by the pressurizer 6 and injected into the inner cavity 82, and the first driver 812 and second driver may be activated to agitate the liquid substrate.

At step S3, the EO-containing sterilization exhaust gas may be injected into the inner cavity 82, passing through the first gas distributor 89, the second gas distributor 87, and the filter screen 86 from bottom to top, and is uniformly dispersed into liquid substrate of the inner cavity 82, wherein the primary stirrer 85 and the secondary stirrer 84 stir in opposite rotational directions to bring the EO-containing sterilization exhaust gas. Thus, the EO-containing sterilization exhaust gas may be brought into contact with the liquid substrate and mixed uniformly. In some of the examples, the treatment progress in the reaction column 8 may be monitored in real-time through the top viewer 81 and/or the side-wall viewer 83.

At step S4, the valve 1310 may be opened to allow the treated gas to be discharged through the gas outlet pipe 9. Treated gas may refer to the resulting gas produced by treatment of the EO-containing exhaust gas as described above, after it has been passing through the liquid substrate. As previously described, the EO concentration of the treated sterilization exhaust gas may be detected with the first EO concentration detector 32 gas, and a flow rate of the treated gas is controlled by the first flow meter 52 to complete discharge. At the same time, the valve 138 and the valve 139 may be opened, and coolant injected into the sandwich chamber 810 through the coolant inlet pipe 10. Coolant may be discharged from the sandwich chamber 810 via the coolant outlet pipe 11, and may be circulated to cool the reaction column 8. The valve 1311 and the valve 136 may be opened and the waste liquid (e.g., spent liquid substrate) may be discharged from reaction column 8 via the liquid outlet pipe 7.

In some examples, when the liquid substrate is injected into the inner cavity 82 of the reaction column 8, in step S1, an operator may observe the liquid level position from the top viewer 81 and/or the side-wall viewer 83, and stop the injection when as the liquid level approaches the junction between the cylindrical body 802 and the upper sealing cover 801.

As previously described, in some embodiments, the liquid substrate may be a liquid acid substrate, such as the ethylene oxide catalytic concentrate.

According to some embodiments, EO in the EO-containing sterilization exhaust gas may be efficiently treated by physical adsorption and chemical reaction of with the liquid acid substrate to generate alcohol, reducing environmental pollution. The embodiments described above may be applicable to decontamination treatment of sterilization exhaust gas containing EO, and provide a simple to operate, safe, and reliable treatment process.

The following examples describe specific implementations of the above-mentioned method for treating EO-containing sterilization exhaust gas.

The EO in the following examples may be industrial EO with a purity of 99.99%. The nitrogen gas may be industrial nitrogen gas with a purity of 99.9%. The acid substrate may be ethylene oxide catalytic concentrate, which is an industrial product.

According to some examples, a method for detecting EO content in exhaust gas may comprise the following procedures and tools:

(1) Gas chromatographic detection: Sampling detection;

Instrument: Gas chromatograph Agilent 7890B;

Column: FFAP quartz capillary column (25 m×0.25 mm×0.25 μm);

Temperature: keep column temperature at 45° C. for 7 min, ramp at 15° C./min to 120° C., hold for 7 min; injection port 130° C., detector 150° C.; Carrier gas: Nitrogen gas 2 mL/min, hydrogen gas 35 mL/min, air 400 mL/min; Injection: Autosampler, gas sample of 1 mL; and Detector: Hydrogen flame detector FID.

(2) EO concentration detector: On-line real-time detection of EO gas concentration in the pipeline;

Instrument: Online EO concentration detector thermal conductance MIC-500s-ETO (0-99% Vol, resolution 0.01% Vol);

Stationary EO detection and alarm device electrochemical JSA5-ETO-AX (0-100 ppm, resolution 0.01 ppm);

Online EO concentration detector PID (0-2000 ppm, resolution 0.1 ppm).

Example 1

The following example provides a method for treating EO-containing sterilization exhaust gas, comprising the steps of:

Step S1: the lower sealing cover 803 was coupled to the cylindrical body 802 by a sealing gasket and a flange, forming a seal with the bottom of the cylindrical body 802. ethylene oxide catalytic concentrate was injected into the inner cavity 82 of the reaction column 8, and the upper sealing cover 801 was similarly coupled to the cylindrical body 802 by a sealing gasket and a flange, forming a seal with the top of the cylindrical body 802.

Step S2: the EO sterilizer 1 was evacuated by the first gas extractor 22, and the valves 134, 135, and 137 were opened while the remaining valves were all kept closed. After the sterilizer 1 was evacuated, the valves 131 and 133 were opened while the remaining valves were all kept closed. EO and nitrogen gas were injected into the sterilizer 1 through the input pipe 4. Valve 131 was closed, and valve 132 was opened, allowing the sterilizing gas to be circulated by the second gas extractor 21. Thus, the sterilizing gas was a mixture of EO, and nitrogen acting as a diluent. The concentration of EO in the mixed sterilizing gas in the sterilizer 1 was detected by the second EO concentration detector 31, and the EO concentration in the sterilizer 1 was controlled by adjusting the input amount of EO and nitrogen gas.

Step S3: when EO-containing sterilization exhaust gas was generated from sterilization process of the sterilizer 1, which is mainly the mixture of EO and nitrogen gas, valves 134, 135, 137, and 1310 were opened while the remaining valves were all kept closed. The EO-containing sterilization exhaust gas in the sterilizer 1 was extracted by the first gas extractor 22, which was pressurized by the pressurizer 6 and then injected into the inner cavity 82 of the reaction column 8. The first driver 812 and the second driver were turned on, and the flow rate of the EO-containing sterilization exhaust gas was regulated by the second flow meter 51.

S4: the sterilization exhaust gas was injected into the inner cavity 82 and passed through the first gas distributor 89, the second gas distributor 87, and the filter screen 86 from bottom to top and be uniformly dispersed into the inner cavity 82, where the primary stirrer 85 and the secondary stirrer 84 rotated clockwise and counterclockwise, respectively, bringing the EO-containing sterilization exhaust gas into contact with and mixed with the liquid ethylene oxide catalytic concentrate. In some of the examples, the treatment process in the reaction column 8 may be visually monitored in real-time through the top viewer 81 and side-wall viewer 83. Meanwhile, the valve 1310 of the gas outlet pipe 9 was opened to allow the treated gas to be discharged through gas outlet pipe 9. The EO concentration of the treated gas was detected by the first EO concentration detector 32, the flow rate of the treated gas was controlled by the first flow meter 52, until evacuation of the reaction column 8 was completed. After the treatment was completed, input of the EO-containing sterilization exhaust gas was stopped. At the same time, the valves 138 and 139 were opened to introduce coolant, in this example cooled water between 20-30° C., continuously into the sandwich chamber 810 through the coolant inlet pipe 10, which was circulated to continuously cool the reaction column 8. The cooling water was discharged from the sandwich chamber 810 from the coolant outlet pipe 11. The waste liquid of ethylene oxide catalytic concentrate, after treatment in the inner cavity 82, was discharged through the liquid outlet pipe 7.

Example 2

With reference to Example 1, in step S2, when the sterilizing gas was circulated by the second extractor 21 and the EO concentration in the mixed gas in the EO sterilizer 1 was detected by the second EO concentration detector 31. In some embodiments, samples may be taken by a sampling device and a composite membrane gas sampling bag. The EO concentration in the EO sterilizer 1 detected by the gas chromatograph was up to 44.38% by volume (% Vol). In step S4, the EO concentration of the treated gas may be detected by the first EO concentration detector 32, sampled by a sampling device and a composite membrane gas sampling bag, and the EO concentration in the treated exhaust gas was detected by the gas chromatograph. Results of the chromatograph analysis are shown in FIG. 8.

Figure 8:
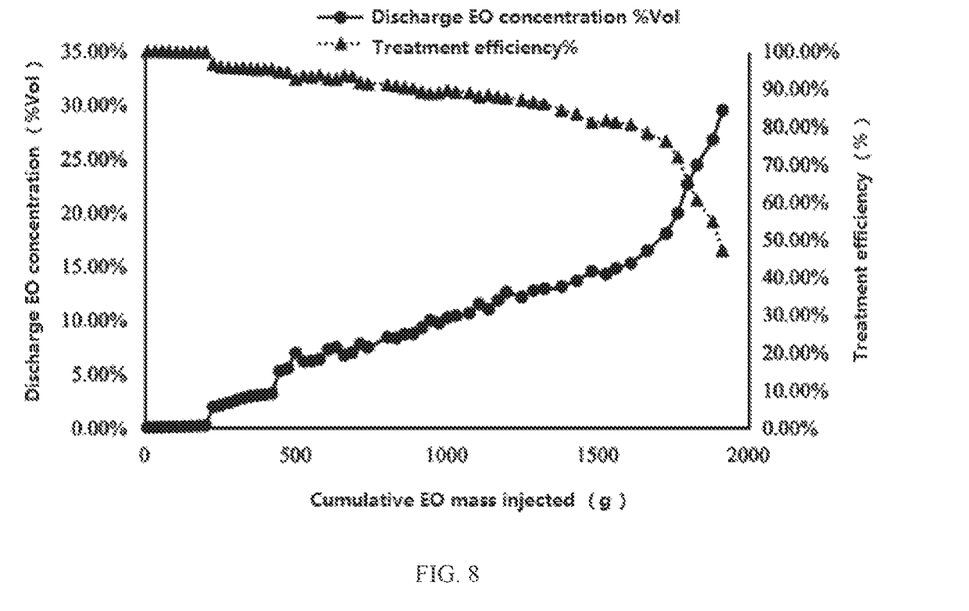
FIG. 8 is a graph showing results of treatment of ethylene oxide-containing sterilization exhaust gas according to an embodiment of the present disclosure.

As can be seen from FIG. 8, after the EO-containing sterilization exhaust gas having an EO concentration of 44.38% Vol had been treated with ethylene oxide catalytic concentrate as the liquid substrate in the reaction column 8, the real-time EO concentration in the treated gas discharged from the reaction column 8 was monitored on-line by the first EO concentration detector 32. At the early stage of the treatment, most of the EO in the sterilization exhaust gas was treated with ethylene oxide catalytic concentrate, the EO treatment efficiency was high, and the EO concentration discharged in the treated gas was low. As the EO-containing sterilization exhaust gas injected into the inner cavity 82 of the reaction column 8 increased, so were the cumulative amount of treated EO by the ethylene oxide catalytic concentrate and the EO concentration in the treated gas, and the treatment efficiency gradually decreased. The EO concentration in the treated gas at an initial time was detected by gas chromatography at about 200 ppm, and the treatment efficiency reached 99.9% or more. When the EO concentration in the treated gas reached 2000 ppm, the treatment efficiency was 99% or more, and the treated EO was 4.31% of ethylene oxide catalytic concentrate by mass. When the EO concentration in the treated gas (also referred to "discharge EO concentration") reached 10.08% Vol, the treatment efficiency was 87% or more, and the cumulative amount of treated EO accounted for 13.18% of the ethylene oxide catalytic concentrate by mass. When the EO concentration in the treated gas reached 29.24% Vol, the cumulative amount of treated EO accounted for 33.34% of the ethylene oxide catalytic concentrate by mass.

Example 3

Continuing with reference to Example 1, in step S2, the sterilizing gas was circulated by the second extractor 21 and EO concentration in the mixed gas in the EO sterilizer 1 was detected by the second EO concentration detector 31. The EO concentration in the sterilizer 1 may be detected by the gas chromatograph by sampling with a sampling device and a composite membrane gas sampling bag, and the EO concentration was detected to be 5.26% Vol. In the above-mentioned step S4, the EO concentration of the treated gas may be detected by the first EO concentration detector 32, and at the same time, the EO concentration in the treated gas may be detected by the gas chromatograph by sampling with a sampling device and a composite membrane gas sampling bag and the results are as shown in FIGS. 9 and 10.

Figure 9:
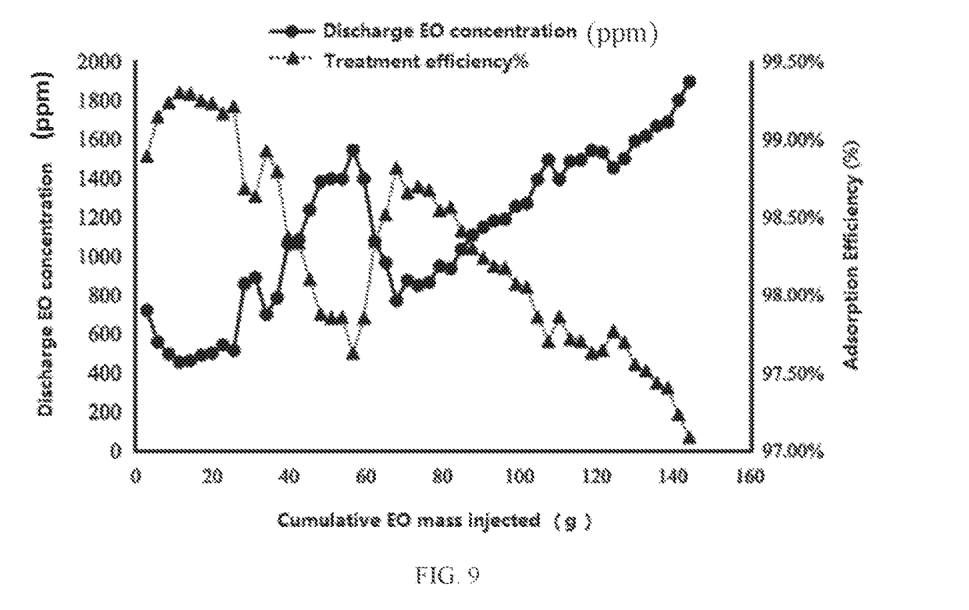
FIG. 9 is a graph showing results of treatment of ethylene oxide-containing sterilization exhaust gas according to an embodiment of the present disclosure.

As can be seen from FIG. 9, after the EO-containing sterilization exhaust gas with an EO concentration of 5.26% Vol was treated with ethylene oxide catalytic concentrate in the reaction column 8, the real-time EO concentration in the treated gas was monitored on-line by an EO concentration detector. It was found that the trend at the early stage of treatment was approximately similar to the EO concentration in the treated gas of EO-containing sterilization exhaust gas at an EO concentration of 44.38% Vol. When the EO concentration in the treated gas was less than 2000 ppm, the treatment efficiency was 97% or more, and the EO absorbed was 5.43% of ethylene oxide catalytic concentrate by mass. The increases and decreases in the EO concentration in the treated gas during the treatment were mainly due to the increases and decreases in the rotational speed of the stirrers and the speed of the chemical reaction itself. When the ethylene oxide catalytic concentrate was used as a catalyst to treat EO by polymerization, the concentration of the synthesized substrate gradually decreases, so does the reaction rate, and the EO concentration of treated gas discharge increases. With the completion of the reaction of the liquid substrate with low polymerization degree, and corresponding increased concentration of substrate with high polymerization degree, the reaction speed of EO picks up again, and the EO concentration of the treated gas is decreased.

Figure 10:
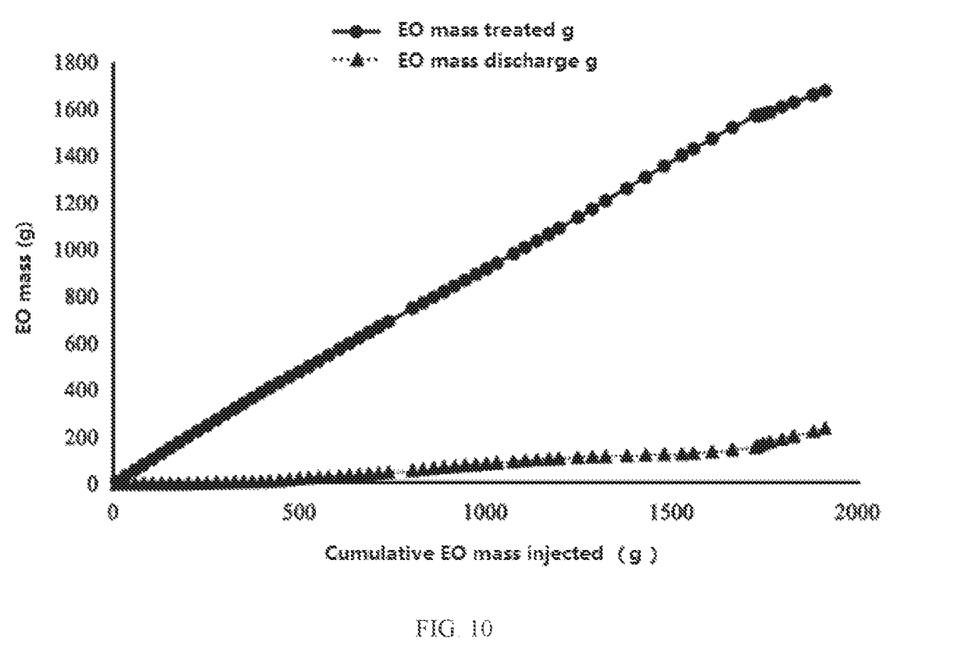
FIG. 10 is a graph showing results of treatment of ethylene oxide-containing sterilization exhaust gas according to an embodiment of the present disclosure.

As can be seen from FIG. 10, the initial rate of EO treatment with ethylene oxide catalytic concentrate is very fast, and the curve of the amount of EO treated shows a quickly increasing trend, with little EO discharged and a gentle curve. As mass of injected EO increases and the cumulatively treated EO approaches saturation of the ethylene oxide catalytic concentrate, the treatment speed of EO is slowed and the amount of EO treated is decreased. The curve showing the amount of EO treated tending to be flat, and the amount of discharged EO (e.g., untreated EO) increased, with the curve of the amount of EO discharged rising rapidly. At the same time, the viscosity of the ethylene oxide catalytic concentrate was measured before and after the treatment. Before the EO treatment, the initial measured viscosity of the ethylene oxide catalytic concentrate was 1050 mPa·s, while after the treatment, the viscosity coefficient of the mixed substrate was reduced to 60 mPa·s. The reduced viscosity of the sulfonic acid may be explained by the fact that the ethylene oxide catalytic concentrate reacted with EO to produce alcohol, in which the ethylene oxide catalytic concentrate is soluble, thereby decreasing the viscosity coefficient of the liquid substrate.

According to the systems for treating EO-containing sterilization exhaust gas provided in the above embodiments, EO in the sterilization exhaust gas may be removed by using an acid to adsorb ethylene oxide and chemically react with EO to produce alcohol. The reaction column may include two gas distributors, a filter screen, and two stirrers, so that the acid substrate and the sterilization exhaust gas can be dispersed and mixed evenly and sufficiently contacted to improve the treating performance. The inside of the reaction column can be observed in real time through the top viewer and the side-wall viewer. Circulating water may be passed through a sandwich chamber to circularly cool the reaction column. The EO concentration detector is capable of detecting EO concentration in the gas before and after treatment. The treatment system provided in the examples of the present disclosure is able to successfully treat the EO-containing sterilization exhaust gas to reduce environmental pollution. The treatment system is applicable to decontamination treatment of EO-containing sterilization exhaust gas, with simple operation, safe process, and good performance, which is advantageous for popularization and application of EO sterilization.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system for treating ethylene oxide-containing sterilization exhaust gas, comprising a reaction column, wherein the reaction column comprises:
    a column body further comprising:
        an inner cavity configured to contain a liquid substrate;
        a bottom portion, the bottom portion further comprising a gas inlet pipe and a liquid outlet pipe, wherein the gas inlet pipe is configured to inject the ethylene oxide-containing sterilization exhaust gas into the inner cavity and the liquid outlet pipe is configured to discharge the liquid substrate from the inner cavity; and
        a top portion further comprising a gas outlet pipe, wherein the gas outlet pipe includes a gas inlet that is above a liquid level of the liquid substrate; and
    at least one gas distributor disposed in the inner cavity of the column body, wherein the at least one gas distributor is disposed above a gas outlet of the gas inlet pipe, wherein the at least one gas distributor is configured to disperse the ethylene oxide-containing sterilization exhaust gas injected from the gas inlet pipe into the inner cavity, wherein the at least one gas distributor comprises a first gas distributor, the first gas distributor being a curved plate, wherein the curved plate includes a plurality of first air holes disposed in an annular arrangement, and the gas inlet pipe is in pneumatic communication with the gas outlet pipe through the plurality of first air holes, and wherein the size of air hole of the plurality of first air holes gradually increases moving in a direction from the center to the edge of the curved plate, wherein the at least one gas distributor further comprises a second gas distributor, wherein the second gas distributor is a flat plate with an edge connected to a side wall of the inner cavity and located above the curved plate, wherein the flat plate further comprises a plurality of second air holes disposed in an annular arrangement, wherein second air holes have a uniform hole pitch from the center to an intermediate region between the center and the edge of the flat plate, while second air holes gradually increase in hole pitch moving in a direction from the intermediate region to the edge of the flat plate.

2. The system according to claim 1, wherein the center of the curved plate is closer to the top portion of the column body and the edge of the curved plate is closer to the bottom portion of the column body, wherein the edge of the curved plate is connected to a bottom wall of the inner cavity.

3. The system according to claim 1, wherein a hole pitch of the plurality of first air holes gradually increases moving in a direction from the center to the edge of the curved plate.

4. The system according to claim 1, wherein the reaction column further comprises a filter screen located in the inner cavity, wherein the filter screen is removably coupled to the side wall of the inner cavity and disposed above the at least one gas distributor.

5. The system according to claim 4, wherein the reaction column further comprises at least one stirrer disposed in the inner cavity, wherein the at least one stirrer is located above the filter screen.

6. The system according to claim 5, wherein the at least one stirrer comprises a primary stirrer coupled to a first rotating shaft, the first rotating shaft further comprising a first upper end that extends out of the column body and is coupled to a first driver.

7. The system according to claim 6, wherein the at least one stirrer further comprises a secondary stirrer, wherein the secondary stirrer is located above the primary stirrer and coupled to a second rotating shaft, wherein the second rotating shaft comprises a second upper end that extends out of the column body and is coupled to a second driver, and wherein the second rotating shaft is disposed coaxially with the first rotating shaft.

8. The system according to claim 7, wherein the primary stirrer has a first rotation direction that is opposite to a second rotation direction of the second stirrer.

9. The system according to claim 1 wherein a first driver and a second driver are configured to selectively connect to a first rotating shaft or a second rotating shaft using a mechanical coupling provided between the first rotating shaft and the second rotating shaft, and wherein the first rotating shaft and the second rotating shaft are connected to a primary stirrer and a secondary stirrer, respectively.

10. The system according to claim 1, wherein a first flow meter and a first ethylene oxide concentration detector are coupled to the gas outlet pipe.

11. The system according to claim 1, wherein the column body further comprises:
    a sandwich chamber surrounding the inner cavity; and
    a coolant inlet pipe and a coolant outlet pipe in communication with the sandwich chamber.

12. The system according to claim 11, further comprising a cooling device configured to cool the column body of the reaction column, wherein the cooling device is connected to the coolant inlet pipe and the coolant outlet pipe.

13. The system according to claim 12, wherein the cooling device includes a water storage tank, a water pump, and a circulating water pipe, wherein the circulating water pipe couples the coolant inlet pipe and the coolant outlet pipe, respectively, to the water storage tank, and wherein the water pump is coupled to the circulating water pipe.

14. The system of claim 1, wherein the liquid substrate is an ethylene oxide catalytic concentrate.

15. The system of claim 14, wherein the ethylene oxide catalytic concentrate is configured to catalyze ethylene oxide waste gas to synthesize ethylene glycol, or to combine with ethylene oxide waste gas to produce a compound complex, wherein the ethylene oxide catalytic concentrate comprises at least one of inorganic acids, sulfonic acids, or unsaturated fatty acids.

16. The system according to claim 1, wherein the column body comprises at least one of a top viewer or a side-wall viewer.

17. The system according to claim 1, further comprising a sterilizer defining an inner volume, wherein the sterilizer further includes an output port coupled to the gas inlet pipe, and a gas inlet connected to an input pipe configured to inject ethylene oxide-containing sterilizing gas into the inner volume of the sterilizer, wherein the ethylene oxide-containing sterilization exhaust gas generated by the sterilizer is discharged from the output port into the gas inlet pipe.

18. The system according to claim 17, wherein the gas inlet pipe is coupled, in sequence along a direction of flow, to a second flow meter, a first gas extractor and a pressurizer.

19. The system according to claim 17, wherein the sterilizer further includes a gas circulation line coupled to the gas inlet and a gas outlet of the sterilizer, respectively, wherein the gas circulation line is further coupled to a second gas extractor and a second ethylene oxide concentration detector.

20. A method of treating ethylene oxide-containing sterilization exhaust gas, comprising:
   providing a reaction column comprising an inner cavity;
   providing a liquid substrate within the inner cavity of the reaction column, wherein the reaction column further includes a gas outlet pipe which includes a gas inlet disposed above a liquid level of the liquid substrate, and at least one gas distributor disposed below the liquid level of the liquid substrate;
   injecting ethylene oxide-containing sterilization exhaust gas into a gas inlet pipe;
   pressurizing, via a pressurizer, the ethylene oxide-containing sterilization exhaust gas in the gas inlet pipe;
   injecting the pressurized ethylene oxide-containing sterilization exhaust gas into the inner cavity, wherein the ethylene oxide-containing sterilization exhaust gas is brought into contact with the liquid substrate, and wherein injecting the pressurized ethylene oxide-containing sterilization exhaust gas into the inner cavity further comprises dispersing, via the at least one gas distributor, the ethylene oxide-containing sterilization exhaust gas in the inner cavity;

discharging, via the gas outlet pipe, the ethylene oxide-containing sterilization exhaust gas that has passed through the liquid substrate; and discharging the liquid substrate through a liquid outlet pipe of the reaction column, when treatment capacity of the liquid substrate for the ethylene oxide-containing sterilization exhaust gas is reduced to a threshold level of catalyzing effectiveness;

wherein the at least one gas distributor comprises a first gas distributor, the first gas distributor being a curved plate, wherein the curved plate includes a plurality of first air holes disposed in an annular arrangement, and the gas inlet pipe is in pneumatic communication with the gas outlet pipe through the plurality of first air holes, and wherein the size of air hole of the plurality of first air holes gradually increases moving in a direction from the center to the edge of the curved plate, wherein the at least one gas distributor further comprises a second gas distributor, wherein the second gas distributor is a flat plate with an edge connected to a side wall of the inner cavity and located above the curved plate, wherein the flat plate further comprises a plurality of second air holes disposed in an annular arrangement, wherein second air holes have a uniform hole pitch from the center to an intermediate region between the center and the edge of the flat plate, while second air holes gradually increase in hole pitch moving in a direction from the intermediate region to the edge of the flat plate.

* * * * *